United States Patent [19]
Brownell et al.

[11] Patent Number: 5,911,988
[45] Date of Patent: Jun. 15, 1999

[54] METHOD FOR TREATING ASTHMA USING SCF ANTIBODY

[75] Inventors: Elise Brownell, Lafayette, Calif.; Nicholas Lukacs, Harland, Mich.; Steven L. Kunkel; Robert M. Strieter, both of Ann Arbor, Mich.

[73] Assignees: Bayer Corporation, West Haven, Conn.; Univ. of Michigan, Ann Arbor, Mich.

[21] Appl. No.: 08/912,541

[22] Filed: Aug. 18, 1997

Related U.S. Application Data

[63] Continuation of application No. 08/431,314, Apr. 28, 1995, abandoned.

[51] Int. Cl.[6] .................................................. A61K 39/395
[52] U.S. Cl. ................................... 424/145.1; 424/152.1; 424/158.1; 424/172.1; 530/388.23; 530/389.2
[58] Field of Search ............................ 424/139.1, 145.1, 424/152.1, 158.1, 172.1; 435/69.7, 70.21, 172.3; 530/351, 387.9, 388.23, 384.2

[56] References Cited

U.S. PATENT DOCUMENTS 5,324,510  6/1994  Wegner et al. ........................ 424/85.8

FOREIGN PATENT DOCUMENTS

WO 92/17505  10/1992  WIPO.

OTHER PUBLICATIONS

Lukacs, Strieter, Warmington, Lincoln, Chensue and Kunkel, 1997, "Differential Recruitment of Leukocyte Populations and Alteration in Airway Hyperreactivity by C—C Family Chemokines in Allergic Airway Inflammation" The Journal of Immunology, 158:4398–4404.

Lukacs, Strieter, Shaklee, Chensue and Kunkel, 1995, "Macrophage inflammatory protein–1α influences eosinophil recruitment in antigen–specific airway inflammation" European Journal of Immunology, 25:245–251.

Lukacs, Strieter, Chensue, Widmer and Kunkel, 1995, "TNF–α Mediates Recruitment of Neutrophils and Eosinophils During Airway Inflammation" The Journal of Immunology, 154:5411–5417.

Lukacs, Strieter, Lincoln, Brownell, Pullen, Schock, Chensue, Taub and Kunkel, 1996, "Stem Cell Factor (c–kit Ligand) Influences Eosinophil Recruitment and Histamine Levels in Allergic Airway Inflammation" The Journal of Immunology, 1996, 156:3945–3951.

Lukacs, Strieter, Chensue and Kunkel, 1996, "Activation and regulation of chemokines in allergic airway inflammation" Journal of Leukocyte Biology 59:13–17.

John Morley, 1993, "Immunopharmacology of asthma" *Trends in Phar. Sci.* 14:208.

C.P. Page, 1993, "An Explaination of the Asthma Paradox" *Am. Rev. Respir. Dis.* 147:S29–S32.

Mark Windt, 1991, "Asthma: Evolving Therapeutic Regimens" *Spectrum Pharmaceuticals Decision Resources, Inc.,* Nov. 4, 1991, pp. 23–1 to 23–7.

Ratko Djukanovic, 1993, "Mechanisms of Airways Inflamation Which May Be Amenable to Prophylaxis" *AAS 40 Update on Childhood Asthma* pp. 169–180.

S. Godfrey, 1993, "Airway Inflammation, Bronchial Reactivity And Asthma" *AAS 40 Update on Childhood Asthma* pp. 109–143.

S. Galli et al., 1993, "The c–kit Receptor, Stem Cell Factor, and Mast Cells" *Am. Jour. Pathobio.* 142(4):965–974.

Kenneth Kaushansky, 1992, "Structure–Function Relationships of the Hematopoietic Growth Factors" *Proteins:Structure, Function, and Genetics* 12:1–9.

(List continued on next page.)

*Primary Examiner*—Sheela Huff
*Assistant Examiner*—Julie E. Reeves
*Attorney, Agent, or Firm*—McDonnell Boehnen Hulbert & Berghoff

[57] ABSTRACT

This invention provides pharmaceutical compositions comprising anti-SCF antibodies for the reduction of eosinophila in the lungs of mammals. This invention also provides for methods of treating asthma and generating a murine model for asthma.

3 Claims, 10 Drawing Sheets

OTHER PUBLICATIONS

Y. Tsuura et al., 1994, "Preferential localization of c–kit product in tissue mast cells, basal cells of skin, epithelial cells of breast, small cell lung carcinoma and seminoma/dysgerminoma in human: immunohistochemical study on formalin–fixed, paraffin–embedded tissues" *Virchows Archiv* 424:135–141.

J.J. Ryan et al., 1994, "Role for Stem Cell Factor/KIT complex in Schwann Cell Neoplasia and Mast Cell Proliferation Associated with Neurofibromatosis" *J. Neurosci. Research* 37:415–432.

Peter Valent, 1994, "The Riddle of the Mast Cell:kit(CD117)–ligand as the missing link?" *Immunology Today*.

A. Iemura et al., 1994, "The c–kit Ligand, Stem Cell Factor, Promotes Mast Cell Survival by Suppressing Apoptosis" *Am. J. Pathobiology* 144(2):321–328.

S. Galli et al., 1993, "Reversible Expansion of Primate Mast Cell Populations In Vivo by Stem Cell Factor" *J. Clin. Invest.* 91:148–151.

T. Kinashi et al., 1994, "Steel factor and c–kit regulate cell–matrix adhesion" *Blood* 83(4):1033–1038.

J. Dastych et al., 1994, "Stem Cell Factor induces mast cell adhesion to fibronectin" *J. of Immunology* 152:213–219.

M–L Li et al., 1993, "Co–stimulatory effects of steel factor, the c–kit ligand, on purified human hematopoietic progenitors in low cell density culture" *Nouv Rev Fr Hematologie* 35:81–86.

A. Dvorak et al., 1993, "Human and Murine Recombinant c–kit ligands support the development of human mast cells from umbilical cord blood cells: ultrastructural identification" *Int Arch Allergy Immunology* 101:247–253.

H. Broxmeyer et al., 1991, "The Kit receptor and its ligands, Steel Factor, as regulators of hemopoiesis" *Cancer Cells* 3(12):480–487.

H. Saito et al., 1994, "Growth in methylcellulose of human mast cells in hematopoietic colonies stimulated by steel factor, a c–kit ligand" *Int Arch Allergy Immunology* 103:143–151.

A. Dvorak et al., 1993, "Ultrastructural morphology of immature mast cells in sequential suspension cultures of human cord blood cells supplemented with c–kit ligand; distinction from mature basophilic leukocytes undergoing secretion in the same cultures" *J. Leukocyte Biology* 54:465–485.

M. Rottem et al., 1993, "The Effects of Stem cell factor on the ultrastructure of $Fc\epsilon R1^+$ cells developing in IL–3–Dependent Murine Bone marrow–derived cell cultures" *J. Immunology* 151:4950–4963.

I. Ziegler et al., 1993, "In a Concerted Action Kit Ligand and Interleukin 3 Control the Synthesis of Serotonin in Murine Bone Marrow–derived Mast Cells" *J. Biol. Chem.* 268(17):12544–12551.

A. Ando et al., 1993, "Effects of Chronic Treatment with the c–kit ligand, Stem Cell Factor, on Immunoglobulin E–dependent Anaphalaxis in Mice" *J. Clin. Invest.* 92:1639–1649.

V. Ackerman et al., 1994, "Detection of Cytokines and Their Cell Sources in Bronchial Biopsy Specimens From Asthmatic Patients" *Chest* 105:687–696.

N. Lukacs et al., 1994, "Interleukin–4–dependent Pulmonary Eosinophil Infiltration in a Murine Model of Asthma" *Am. J. Respir. Mol. Biol.* 10:526–532.

Genzyme Catalog 1993 pp. 196–199.

Chester et al 1995 Tibtech vol. 13:294–300.

Durum et al 1993 Fundamental Immunology Ch 21.

Bischoff et al. 1992 J. Exp. Med. 175:237–244.

METHOD FOR TREATING ASTHMA USING SCF ANTIBODY

This application is a continuation of application Ser. No. 08/431,314, filed on Apr. 28, 1995, now abandoned.

BACKGROUND OF THE INVENTION

1. Field of the Invention

This invention relates to pharmaceutical compositions comprising antibodies or fragments thereof which are specific for Stem Cell Factor (SCF), and methods for testing and using such pharmaceutical compositions in a defined dose range to alleviate asthma and related inflammatory disease in mammals.

2. Description of the Prior Art

Asthma is a lung disease characterized by (1) airways obstruction that is reversible (but not completely in some patients), either spontaneously or with treatments, (2) airways inflammation, and (3) increased airways responsiveness to a variety of stimuli. Asthma involves airways obstruction which is due to a combination of factors that include (1) spasm of airways smooth muscle; (2) edema of airways mucosa; (3) increased mucus secretion; (4) cellular, especially eosinophilic, infiltration of the airways walls; and (5) injury and desquamation of the airways epithelium. (see generally *The Merck Manual of Diagnosis and Therapy*, 7th edition, Berkow, R. ed., Merck Research Laboratories, Rahway, N.J. 1992, chp. 34). About 10 million asthmatics live in the United States. From 1980 to 1987 there has been a 29% increase in the prevalence rates of asthma, and from 1970 to 1987 hospital discharge rates for asthma nearly tripled. More alarmingly, the mortality rate from asthma worldwide is increasing, in the United States alone increasing 37% from 1980 to 1987.

The alleviation or prevention of asthma related inflammation is highly desirable, for both human reasons and as an adjunct to proper effective clinical management of asthmatic disease. Aside from prophylactic steps to minimize exposure to certain environmental factors, and nonspecific exacerbating factors, treatment of asthma is conveniently considered as management of the acute attack and day-to-day therapy. Conventional methods of treatment can be classified under five groups of drug therapies: β-adrenergic agents, theophylline, corticosteroids, cromolyn sodium and anticholinergic agents. (M. Windt, 1991, "Ashma: Evolving Therapeutic Regimens", *SPECTRUM Phamaceuticals*, Decision Resources, Inc., pp23-1 to 23-7).

β-Adrenergic agents (β1 and β2) are useful for treating acute asthma attacks, or to prevent acute attack after exercise, because of their rapid onset (usually within minutes),and relatively short duration (4 to 6 hours at most). It is believed that unfortunately, treatment with β2-adrenergic agents alone, may in fact potentiate hyperresponsiveness and thereby make patients more susceptible to asthma attack. (C. P. Page, 1993, "An Explanation of the Asthma Paradox", *Am Rev Respir Dis* 147:S29–S32). Adverse effects are more common after oral administration than aerosol, because of the general effects on smooth and cardiac muscles. Theophylline (a methylxanthine) also relaxes smooth muscle, but does not inhibit mediator release by granulocyte, nor does it inhibit hyperresponsiveness following antigen challenge or long-term use. Corticosteroids are general anti-inflammatory agents which inhibit the attraction of polymorphonuclear leukocytes to the site of allergic reaction. Long term therapy can decrease bronchial hyperresponsiveness (especially after aerosol administration). Systemic corticosteroids are very effective, but are reserved for more difficult acute episodes because of the many potential adverse effects. Cromolyn sodium (DSCG, disodium cromoglycate), used prophylactically appears useful in treating children and some adults, as maintenance therapy. It is not suitable for treating acute attacks. In the United States, cost and problems with patient compliance has limited its use, even though this is the safest drug available for the treatment of asthma. Anti-cholinergic agents block cholinergic pathways that cause airway obstruction and may provide additional bronchodilator effect in treating acute attack. Such methods are unsatisfactory because they do not clinically address the source of the inflammatory response, the physiological problem which leads to asthmatic sensitivity, and because of the side effects of such powerful drugs on the patient.

The pathophysiology of asthma is marked by an inflammatory state in which the airways are narrowed chronically by edema and episodically by a variety of spasmogens that are released from resident and infiltrating cells. (see generally *Goodman and Gilman's—The Pharmacological Basis of Therapeutics*, 8th edition, Gilman, Rall, Nies, and Taylor eds., Pergamon Press, New York, N.Y., 1990; chp. 25). Asthmatic hyperresponsiveness to chemical and physical stimuli can cause bronchoconstriction almost immediately (immediate response), as well as an episode several hours later (late response). This late response appears to occur due to the recruitment of circulating cells which are attracted to the area by chemotactic factors (mediators), which serve to maintain or intensify the inflammatory state. It is believed that environmental antigens are responsible for maintaining a state of hyperresponsiveness which underlies the asthma of many individuals. The list of known or suspected mediators which may play a role in the allergic responses of asthma have been growing steadily over the years and currently include histamine, prostanoids, leukotrienes, and platelet-activating factor (PAF). Also implicated are the release of acetylcholine and neuropeptides such as substance P from parasympathetic nerves.

Generally, the focus of therapeutic intervention of the mechanisms of asthma has focused on inhibition or antagonism of chemical mediators involved in cell recruitment, potentiation, and maintenance of the hyperresponsive state. Such therapies aim to reduce the activation or accumulation of inflammatory cells in the sensitive regions. (J. Morley, 1993, "Immunopharmacology of asthma", *TiPS* 14:208–213). As appreciation of the complexity of the pathophysiology of asthma has increased, certainty as to the mechanism of action and the cellular targets of therapeutic agents has decreased. This is a major limitation to the use of mediator based pharmaceuticals for treating asthma, which is in addition to the unwanted side effects associated with such treatments. Atopy has become a focus for some researchers, and directs pharmacological intervention of mediators and cells on the immunological/immunogenic basis of asthma. (R. Djkanovic et al., 1993, "Mechanisms of airways inflammation which may be amenable to prophylaxis", *AAS Update on Childhood Asthma* 40:169–180). Many cytokines have been studied with the goal of determining the cell sources. (V. Ackerman et al., 1994, "Detection of cytokines and their cell sources in bronchial biopsy specimens from asthmatic patients", *Chest* 105:687–696). The predominant cells bearing IgE in the late-phase response to antigen in the lung was identified as being basophils in one study focusing on histamine as a key mediator. (C. B. Guo et al., 1994, "Identification of IgE-bearing cells in the late-phase response to antigen in the lung as basophils", *Am J Respir Cell Mol Biol* 10:384–390). Thus, while the focus is still on reduction of hyperreactivity, and reducing inflammation by intervention with the mediator signals, it has been recognized that a reduction in the number of reactive cells will apparently result in reduced inflammation. (S. Godfrey, 1993, "Airway inflammation, bronchial reactivity and asthma", *AAS Update on Childhood Asthma* 40:109–143).

It would, therefore, be advantageous to be able to utilize a pharmaceutical composition and a treatment which produce minimal toxicity or side effects, but provide highly effective, reproducible results yielding a reduction in the number of reactive cells, thereby avoiding the complexity and confusion over therapeutic intervention with mediator signals, by preventing the action of the responsible cells.

It has been shown that stem cell factor (SCF, c-kit ligand, steel factor) critically regulates the migration and survival of mast cell precursors, promotes the proliferation of both immature and mature mast cells, enhances mast cell maturation, directly induces secretion of mast cell mediators, and can regulate the extent of mediator release in mast cells activated by IgE-dependant mechanisms. (S. J. Galli et al., 1993, "The c-kit Receptor, Stem Cell Factor, and Mast Cells", *Am J Pathology* 142:965–974). In addition, SCF is one of the hematopoietic growth factors are a family of glycoproteins involved in the production of blood cells from bone marrow precursors. (K. Kaushansky, 1992, "Structure-function relationships of the hematopoietic growth factors", *Proteins: Structure, Function, and Genetics* 12:1–9). SCF appears to also be a costimulatory factor in many of the hematopoietic cell lines, but required multi-lineage factors such as IL-3 in order to maintain their development. (M-L Li et al., 1993, "Co-stimulatory effects of steel factor; the c-kit ligand, on purified human hematopoietic progenitors in low density cell culture", *Nouv Rev Fr Hematologie* 35:81–86; H. E. Broxmeyer et al., 1991, The Kit receptor and its ligand, steel factor, as regulators of hematopoiesis", *Cancer Cells* 3:480–487; H. Saito et al., 1994, "Growth in methylcellulose of human mast cells in hematopoietic colonies stimulated by steel factor, a c-kit ligand", int *Arch Allergy Immunol* 103:143–151). The action of Kit ligand and IL-3 may control the synthesis of serotonin in mast cells. (I. Ziegler et al, 1993, "In a concerted action Kit ligand and interleukin 3 control the synthesis of serotonin in murine bone marrow-derived mast cells", *J Biological Chem* 268:12544–12551). Interestingly enough, SCF/KIT has been found associated with neurological pathologies as well. (*I. J. Ryan et al.,* 1994, "Role for the Stem Cell Factor/KIT complex in Schwann cell neoplasia and mast cell proliferation associated with neurofibromatosis", *J Neurosci Res* 37:415–432).

It has been found that both murine and human recombinant c-kit ligands are active on human mast cell precursors, indicating that the structure and function is highly conserved if not essentially identical. (A. M. Dvorak et al., 1993, "Human and murine recombinant c-kit ligands support the development of human mast cells from umbilical cord blood cells: ultrastructural identification", *Int Arch Allergy Immunol* 101:247–253).

It appears that SCF has emerged as the key to the riddle of mast cell activity. (P. Valent, 1994, "The riddle of the mast cell: kit(CD-117)-ligand as the missing link?", *Immunology Today* 15:111–114). Recent work has shown that there is localization of the receptor for SCF (c-kit product, KIT) in various tissues. (Y. Tsuura et al., 1994, "Preferential localization of c-kit product in tissue mast cells, basal cells of skin, epithelial cells of breast, small cell lung carcinoma and seminoma/dysgerminoma in human: immunohistochemical study of formalin-fixed, paraffin-embedded tissues", *Virchows Archiv* 424:135–141).

It has been found that the c-kit ligand promotes mast cell survival by suppressing apoptosis. (A. Iemura et al., 1994, "The c-kit ligand, Stem Cell Factor, promotes mast cell survival by suppressing apoptosis", *Am J Pathology* 144:321–328). Treatment with rhSCF (recombinant human SCF) was found to reversibly expand mast cell populations in primates in vivo. (S. J. Galli et al, 1993, "Reversible expansion of primate mast cell populations in vivo by stem cell factor", *J Clin Invest* 91:148–152). SCF and c-kit have been found to regulate cell-matrix adhesion to fibronectin in a transient manner. (T. Kinashi and T. A. Springer, 1994, "Steel factor and c-kit regulate cell-matrix adhesion", *Blood* 83:1033–1038). This adhesion was not dependent on IL-3 and was blocked by antibody to SCF. (J. Dastych and D. D. Metcalfe, 1994, "Stem Cell Factor induces mast cell adhesion to fibronectin", *J Immunology* 152:213–219). Yet final differentiation of mast cell may require interaction with fibroblasts. (A. M. Dvorak et al.,1993, "Ultrastructural morphology of immature mast cells in sequential suspension cultures of human cord blood cells supplemented with c-kit ligand; distinction from mature basophillic leukocytes undergoing secretion in the same cultures", *J Leukocyte Bio* 54:465–485). SCF in the presence of IL-3 increases the ratio of mast cells to basophils and alters the ultrastructural characteristics of mast cells and basophils toward a more mature phenotype. (M. Rottem et al, 1993, *J Immunology* 151:4950–4963).

Work has suggested that rhSCF and anti-IgE may act on human mast cells through a common pathway to increase free cystolic calcium, and that this effect can be similarly modulated by various drugs. (M. Columbo et al., 1994, "Studies of the intracellular Ca2+ levels in human adult skin mast cells activated by the ligand for the human c-kit receptor and anti-IgE", *Biochem Pharmacol* 47:2137–2145). Other work has shown that mast cells potentiate the release of cytokines in response to IgE cross-linking, and perhaps does not act to stimulate release directly. (S. C. Bischoff and C. A. Dahinden, 1992, "c-kit ligand: a unique potentiator of mediator release by human lung mast cells", *J Exp Med* 175:237–244). In contrast, work with rrSCF (recombinant rat SCF) in mice indicates that chronic treatment with rrSCF induced mast cell hyperplasia, but does not increase the severity of IgE-dependent anaphylactic reactions. (A. Ando et al, 1993, "Effects of chronic treatment with the c-kit ligand, Stem Cell Factor, on immunoglobulin E-dependent anaphylaxis in mice", *J Clin Invest* 92:1639–1649).

There have been several patent publications in relation to SCF and c-kit product the SCF receptor.

European patent application 0 548 867 A2, published 30.06.93, teaches a soluble stem cell factor (SCF)-receptor (KIT, c-kit product).

International patent application PCT/US 92/02674, published Oct. 15, 1992, teaches monoclonal antibodies to stem cell factor receptors.

International patent application PCT/US 91/06130, published Mar. 5, 1992, teaches a ligand for the c-kit receptor and methods of use.

UK patent application GB 2 258 234 A, published Feb. 3, 1992, teaches a soluble Kit ligand (KL) protein.

European patent application 0 423 980 A1, published Apr. 24, 1991, teaches stem cell factor and methods of use for treating blood disorders.

International patent application PCT/US 93/03640, published Nov. 11, 1993, teaches ligand for the c-kit receptor and methods of use thereof.

There remains a need in the medical arts for an effective treatment for asthma, and the inflammation that is associated with asthma. Although its importance and use for maintaining cell cultures of hematopoietic stem cells and therapeutic uses in stimulating hematopoiesis is known, SCF has not been shown to be a desirable or effective target for any therapeutic intervention in the treatment of asthma.

As discussed earlier, the pathophysiology of asthma is not clear. The study of the pathophysiology has been hampered by the lack of affordable, uniform, and well characterized animal models for the study of atopic asthma. Atopic asthma in humans has been described as an allergic disease characterized by reversible obstruction of the airways or bronchi. The immune response associated with the onset of asthma has been described as having mixed histopathological features of both acute and chronic, cell-mediated immune reactions. This response is histopathologically characterized by the infiltration of the bronchial mucosa with neutrophils, eosinophils, macrophages, and lymphocytes (see for review C. J. Corrigan and A. B. Kay, 1992, "T cells and eosinophils in the pathogenesis of asthma", *Immunol Today* 13:501–507), though basophils have been indicated as being a source of chemotactic factors. Data on asthma suggests that the onset of the asthmatic response is controlled by CD4+ T-lymphocytes which produce a characteristic TH2 pattern of lymphokine production (A. B. Kay and C. J. Corrigan, 1992, "Asthma, eosinophils and neutrophils", *Br Med Bull* 48:51–64). The TH2 pattern of lymphokines consists of expression of IL-4, IL-5, and IL-10 (Mossman and Moore, 1989, "The role of IL-10 in crossregulation of Th1 and Th2 response", *Immunol Today* 12:A49–A58; Mossmann, T. R. et al., 1986, "Two types of murine helper T cell clone", *J Immunol* 136:2348–2359). The expression of these lymphokines correlates well with asthma as their individual functions play a role in the asthmatic response. The expression of IgE (IL-4) (Zhang, X. et al., 1992, "T cells from atopic individuals produce IgE-inducing activity incompletely blocked by anti-interleukin-4 antibody", *Eur J Immunol* 22:829–833) and eosinophilia (IL-4/IL-5) (Spry, C. J. et al., 1992, "Eosinophils", *Immunol Today* 13:384–387) are both characteristic of asthmatic responses (Del Prete, G., 1992, "Human Th1 and Th2 lymphocytes: their role in the pathophysiology of atopy", *Allergy* 47:450–455). However, a primary trait of asthma is the accumulation of eosinophils in the bronchoalveolar lavage (BAL) fluid (Corrigan and Kay, 1992; Kay and Corrigan, 1992; Arm, J. P. and T. H. Lee, 1992, "The pathobiology of bronchial asthma", *Adv Immunol* 51:323–382; Diaz et al., 1989, "Leukocytes and mediators in bronchoalveolar lavage during allergen-induced late-phase asthmatic reactions", *Am Rev Respir Dis* 139:1383–1389). Historically, eosinophils have been implicated as a primary cell responsible for the induction of bronchial mucosal injury and are thought to induce the bronchial obstruction associated with the asthmatic response (Kay and Corrigan, 1992; Djukanovic et al., 1990, "Mucosal inflammation in asthma", *Am J Respir Dis* 142:434–457; Walker et al., 1993, "Increased expression of CD11b and functional changes in eosinophils after migration across endothelial cell monolayers", *J Immunol* 150:4061–4071). Due to the difficulty of longitudinal studies of patient populations and paucity of asthma-related data in animal models, the mechanisms which lead to the pathophysiology of this disease are not presently clear. It would be most useful to the medical and scientific community to have a murine model to examine the cellular and molecular events involved in the asthmatic response.

In order to develop and test pharmaceutical treatments for asthma, it would be useful to have an appropriate, characterizable, economical and readily available animal model system for the disease. Laboratories have employed, as animal models, the use of various antigens or pharmaceutical agents in dogs and primates as well as guinea pigs (Mapp et al., 1985, "Airway responsiveness to inhaled antigen, histamine, and methacholine in inbred, ragweed sensitive dogs", *Am Rev Respir Dis* 132:292–298; Sasaki et at, 1989, "Late asthmatic response to Ascaris antigen challenge in dogs treated with mtyrapone", *Am Rev Respir Dis* 136:1459–1465; Yamada et al., 1992, "Development of an animal model of late asthmatic response in guinea pigs and effects of anti-asthmatic drugs", *Prostaglandins* 43:507–521). Work with the canine system has not been greatly expanded, and is hampered by the cost of the animals, care, lack of characterized reagents, ease of generating large numbers of genetically identical individuals, and strict regulations.

At present two animal models are mainly being used to study asthma. The first is an *Ascaris suum* parasite antigen-induced primate model system (R. H. Gundel et al., 1992, "Antigen-induced acute and late-phase responses in primates", *Am Rev Respir Dis* 146:369–373; D. I. Pritchard et al., 1983, "Laboratory infection of primates with *Ascaris suum* to provide a model of allergic bronchoconstriction", *Clin Exp Immunol* 54:469–476). There have been major obstacles to the use of this model system, like the canine system, the least of which has been limits of strict regulations and prohibitive cost of the animals.

The second animal model being used is induced in guinea pigs by various antigens (H. Iijima et al., 1987, "Bronchoalveolar lavage and histologic characterization of late asthmatic response in guinea pigs", *Am Rev Respir Dis* 136:922–929; K. Ishida et al, 1989, "Repeated antigen challenge induces airway hyperresponsiveness with tissue eosinophilia in guinea pigs", *J Appl Physiol* 67:1133–1139; C. Vertes et al., 1987, "A model for experimental asthma: provocation in guinea-pigs immunized with *Bordetella perussis*", *Bull Eur Physiopathol Respir* 10:111s–113s), and pharmaceuticals (J. P. Hayes et al, 1992, "Bronchoconstriction and airway microvascular leakage in guinea pigs sensitized with trimellitic anhydride", *Am Rev Respir Dis* 146:1306–1310; H. Obata et al.,1992, "Guinea pig model of immunologic asthma induced by inhalation of trimellitic anhydride", *Am Rev Respir Dis* 146:1553–1558). Unfortunately, there are major difficulties with this system, among them are the limited array of reagents available for the examination of leukocyte subsets and cytokines produced during the asthma reaction. Difficulty and cost of acquiring, breeding, and maintaining the animals is also a deterrent to their use.

Thus there is still a need for a useful model, and method for generating such an animal model for asthma which would have the advantages of reagent availability for characterization of the disease, low cost, and the ability for assessing a large number of genetically similar animals during pathogenesis of airway inflammation compatible with asthma.

The normal immune response to parasite eggs (soluble egg antigen; SEA), and secreted antigen, during parasite infection, has previously been demonstrated to induce a TH2 driven response, which includes high IL-4 levels and a striking eosinophilia (Chensue et al., 1992, "Role of IL-4 and IFN-gamma in *Schistosoma mansoni* egg-induced hypersensitivity granuloma formation", *J Immunol* 148:900–911; Grzych et al., 1991, "Egg deposition is the major stimulus for the production of Th2 cytokines in murine schistosomiasis mansoni", *J Immunol*

146:1322–1329). Presumably the nature of SEA predisposes the immune system to a TH2 type response, (Lukacs and Boros, 1992, "Utilization of fractionated soluble egg antigens reveals selectively modulated granulomatous and lymphokine responses during murine schistosomiasis mansoni", *Infect Immunol* 60:3209–3216; Lukacs and Boros, 1993, "Lymphokine regulation of granuloma formation in murine schistosomiasis mansoni", *Clin Immunol Immunopaht* 68:57–63), which may be exploited for developing a murine model system for asthma.

SUMMARY OF THE INVENTION

The present invention provides a pharmaceutical composition for the treatment of asthma comprising an antibody or biologically active fragment thereof, reactive with SCF, in a suitable carrier for administration to the lung. The instant invention also encompasses a method for treating asthma in mammals, comprising contacting tissue with an effective amount of antibody, or biologically active fragment thereof, reactive with SCF. In a preferred embodiment of the instant invention, the antibody is administered to the lungs.

The instant invention provides a method for modeling asthma in mice, comprising immunizing mice with *Schistosoma mansoni* egg antigen (SEA), waiting for a first incubation period, administering SEA to the airways of the mice, waiting a second incubation period, and then administering SEA to the lungs of the mice. The first incubation period is between 1 and 2 weeks and the second incubation period is from 5 to 8 days. Preferably the first incubation period is 2 weeks and the second incubation period is 6 days. The instant invention also provides for a method for reducing eosinophilia in the lungs of a mammal comprising administering an effective amount of anti-IL4 antibody to the mammal. Further, the instant invention encompasses a method for reducing eosinophilia in the lungs of a mammal comprising administering an effective amount of an anti-SCF antibody to the mammal.

The instant invention also encompasses the use of other, SCF specific agents which can bind and/or inactivate SCF which may be present in asthmatic patients. Such agents can include catalytic antibodies, single-chain antibody constructs, SCF targeted proteases, and other such agents. Thus a key feature of the therapeutic treatment of the instant invention is the inhibition of SCF activity in asthma, either by inactivating SCF, inhibiting SCF, inhibiting SCF binding to SCF target sites, inhibiting SCF receptors, or other methods of disrupting the SCF activity associated with asthma.

Specific preferred embodiments of the present invention will become evident from the following more detailed description of certain preferred embodiments and the claims.

DETAILED DESCRIPTION OF THE INVENTION

Figure 1A:
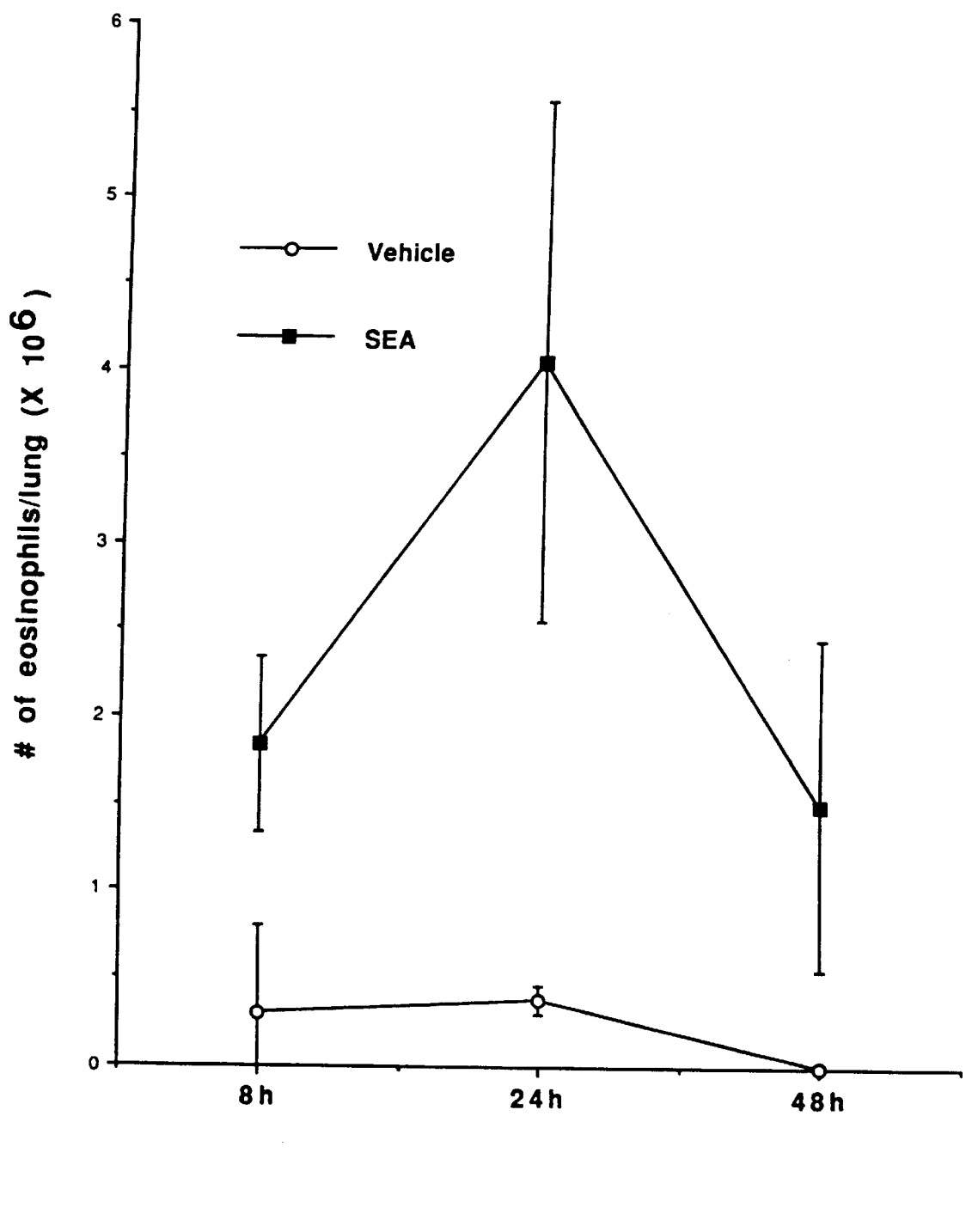
FIG. 1A shows eosinophil infiltration into the lungs and airways. The graph shows eosinophil cell counts from dispersed lungs of SEA and vehicle trachea challenged mice. The collagenase dispersed lung cells were collected at 8, 24, and 48 hours after the antigenic challenge and quantitated by vital dye exclusion. Data represents the mean ±SE(Standard Error) from 3 different mice in each group.

The establishment of a murine model of asthma is important for determining the mechanisms and cellular events which take place during an asthmatic response. In one embodiment of the instant invention, methods are described for making a murine model of airway inflammation using a parasitic antigen (SEA) isolated from *Schistosoma mansoni* eggs (N. Lukacs et al., 1994, "IL-4 dependent eosinophil infiltration in murine asthma", *Am J Resp Cell Mol Biol* 10(5):526–532). The demonstration of IL-4 production and eosinophil influx, substantiates a TH2-driven response in the murine model of the instant invention as being equivalent to human atopic asthma. The cellular response which followed the airway antigen challenge included a rapid influx of neutrophils from 1 to 8 hours followed by a mononuclear and eosinophilic infiltration which peaked 8 to 24 hrs in the lung and 24 to 48 hrs in the airway (BAL). Interestingly, the vehicle control treated mice displayed a smaller yet distinctive early rise in neutrophils at 8 hrs in the airway while no increase in eosinophils was observed. This nonspecific response has been reported in healthy human volunteer BAL fluid, after undergoing bronchoscopy. In addition to validating the murine model of the instant invention, these data suggest two phases of the inflammation process; an early nonspecific neutrophilic response and a later antigen-specific lymphocyte/eosinophil response. Whether the early neutrophil component has a role in inducing the later specific response is presently under investigation. The elevated numbers of peribronchial and BAL eosinophils in the SEA treated lungs is consistent with the airway inflammation observed in human patient populations with asthma, as eosinophil numbers have been used to correlate the clinical severity of asthmatic inflammation. In murine model of the instant invention, the eosinophil influx was causally related to IL-4 production, as the passive immunization of mice with anti-IL-4 antibodies in vivo decreased eosinophil influx by tenfold. These data indicate that IL-4 plays a major role in the asthmatic response presumably by promoting the recruitment and migration of eosinophils to the interstitium and airspace as indicated by dispersed whole lung and BAL samples. This is consistent with previous studies which suggest that asthma is induced by antigen-specific TH2 type responses (Corrigan and Kay, 1992b, "Asthma. Role of T-lymphocytes and lymphokines", *Br Med Bull* 48:72–84; Robinson et al, 1992, "Predominant TH2-like bronchoalveolar T-lymphocyte population in atopic asthma", *N Engl J Med* 326:298–304; Romangnani et al, 1991, "Increased numbers of TH2-like CD4+T cells in target organs and in the allergen-specific repertoire of allergic patients", *Int Arch Allergy Appl Immunol* 94:133–136; Kay, 1991, "T lymphocytes and their products in atopic allergy and asthma", *Int Arch Allergy Appl Immunol* 94:189–193; Walker et at., 1991, "T cells and asthma", *Int Arch Allergy Appl Immunol* 94:248–250). In addition, other studies have identified IL-4-mediated eosinophilia utilizing transfected tumor cells (Tepper et al., 1984, "Murine interleukin-4 displays potent anti-tumor activity in vivo", *Cell* 57:503–512) and transgenic mice (Tepper et al., 1989, "IL-4 induces allergic-like inflammatory disease and alters T cell development in transgenic mice", *Cell* 62:457–467), lending support to our assertion that IL-4 is a primary inducer of the eosinophilic response.

The present model provides a means to study sequential cellular and molecular as well as airway hyperactivity responses in asthmatic lung inflammation with the ability to evaluate potentially therapeutic agents. Other animal models of asthma have also examined the cellular allergic response in the lung, and these models have provided data that would otherwise be unattainable from human patient populations, such as the effects of anti-asthmatic drugs, longitudinal study of airway reactivity after challenge, cellular infiltrations, and examination of late phase asthmatic responses. However, these models have disadvantages that limit their efficacy for characterization of the asthmatic responses. For example, the primate model is not only expensive but also severely regulated, while dog and guinea pig models, although less expensive than primates, are limited by the lack of reagents available to fully characterize the airway immune response. Taken together, a murine model of asthma not only provides the necessary genetic uniformity but also has a wide array of reagents available to effectively study the mechanisms involved in asthmatic reactivity. The data in the present study describes a murine model of airway inflammation which mimics the pathophysiology of human asthma and provides useful information as to the local activation and sequential infiltration of cells into the interstitium of the lung and airway during the antigen-specific response. IL-4 plays a major role in the this airway allergic response and may play a pivotal role in the exacerbation of the inflammatory reaction and eosinophil-induced injury in the lung. This data also suggests that both an early neutrophil and late eosinophilic response may be involved in the pathogenesis of allergic airway inflammation.

Surprisingly, initial attempts to induce an asthma-like cellular infiltration without prior exposures of lung to antigen caused little cellular infiltration. Although there was systemic immunity to SEA, we found that the pulmonary allergen-response required primary localization to the lungs, followed by a secondary challenge several days later. Combined systemic and pulmonary immunity likely occurs in asthmatics, since many are atopic. It is probable, however, that most asthmatics have a local response in the lung prior to systemic sensitization. In the present model it is useful to induce an initial systemic response to SEA with subsequent localization to the lungs in order to provide a consistent method of sensitization.

The following examples illustrate certain aspects of the instant invention and advantageous results, and are shown by way of illustration and not by way of limitation.

EXAMPLE 1

Murine Model for Asthma

The establishment of practical and accurate animal models of human asthma is critical to elucidate the mechanisms involved in the pathogenesis of the disease. In this example a method for establishing a useful animal model for asthma is demonstrated which uses a parasite antigen from *Schistosoma mansoni* eggs, which induces a TH2 response, to elicit a pulmonary inflammatory reaction which resolves after 3–4 days. Histological examination of the lungs of soluble egg antigens (SEA) or saline vehicle challenged mice demonstrated a large influx of cells in the antigen challenged, but not vehicle challenged mice, thus demonstrating an antigen-specific reaction.

Initial attempts to induce an asthma-like cellular infiltration without prior exposures of lung to antigen caused little cellular infiltration. It was found that the pulmonary allergen-response required primary localization to the lungs, followed by a secondary challenge several days later. In the present model the method comprises an initial introduction of antigen to induce an initial systemic response to SEA with subsequent localization to the lungs in order to provide a consistent method of sensitization.

Materials and Methods

Animals. Female CBA/J mice were purchased from Jackson Laboratories, (Bar Harbor, Me.) were maintained under standard pathogen-free conditions.

Egg isolation and SEA protein preparation. Soluble egg antigens (SEA) were prepared from acutely *S. mansoni*-infected mice as previously described (Lukacs and Boros, 1992). Briefly, eggs were isolated from livers of infected mice after a 3 day incubation and ground on ice to release the soluble antigens from the egg. The preparation was then spun in an ultracentrifuge at 100,000×g for 2 hrs and the supernatant collected. The antigens in the supernatant are primarily glycoproteins which have been characterized as inducing a TH2 type granulomatous response in schistosomiasis.

Sensitization and induction of the asthma response. In order to induce a TH2 type response the following procedure was established in normal 5–8 week old CBA/j mice. The mice were immunized with 5000 isolated *S. mansoni* eggs i.p. at days 0 and 7 of the protocol. On day 14 the mice were given an intranasal challenge of 10 $\mu$g of SEA in 10 $\mu$l of PBS to localize the response to the airway.

This initial intranasal challenge with antigen induced little cellular infiltrate into the lungs of the mice, as seen upon histological examination. Mice were then rechallenged six days later intratracheally with 10 $\mu$g of SEA in 25 $\mu$l of sterile PBE; or with PBS alone (vehicle control). The mice were sacrificed at various times after the intratracheal challenge (1, 8, 24, 48, and 72 hrs) and the lungs inflated and fixed in 10% buffered formalin. The magnitude of infiltration in both the vehicle control and SEA challenged mice was examined histologically.

Quantification and differentiation of leukocyte populations in BAL and lungs.

Mice immunized and challenged with SEA or saline vehicle were subjected to a 1 ml bronchial alveolar lavage (BAL) with phosphate buffered saline (PBS) containing 50 mM EDTA at various time points from 8 hrs to 72 hrs post-challenge. The cells were centrifuged out of the BAL, counted, and differentially stained with Wright-Giemsa stain. The cell-free BAL fluid was frozen at $-20°$ C. for later cytokine and antibody analysis. The lungs were removed after the 1 ml PBS-EDTA lavage and dispersed with collagenase (0.2%, Type IV, Sigma) as previously described (Zhang et al., 1992). The dispersed cells were then counted, dispersed using a cytospin and differentially stained with Wight-Giemsa stain. The cell types found, mononuclear phagocytes, lymphocytes, neutrophils, and eosinophils were expressed as a percentage based on 200 total cells counted/sample for both the BAL and dispersed lung cells.

IL-4 assay and in vivo neutralization. Assessment of bioactive IL-4 was quantitated using the IL-4-dependent cell line CT.4S (kindly provided by Dr. William Paul, NIH Bethesda, Md.). The cells were maintained in recombinant murine IL-4 (rmIL-4; R & D) in RPMI 1640 media supplemented with 5% FICS, $10^{-5}$M 2-ME, 2 mM sodium pyruvate, 20 mM L-glutamine, and 1000 U and 100 mg/ml, respectively, of penicillin and streptomycin. The supernatants were diluted and added to $5 \times 10^3$ CT.4S cell/well in RPMI without rmIL-4 in 96 well plates. IL-4 levels were determined by comparison of serially diluted supernatants to a standard curve using rmIL-4.

To determine the role of IL-4 in the murine asthma model we injected anti-IL-4 polyclonal antibodies (250 μg/mouse; R&D, Minnesota, Minn.) i.p. into immunized mice 2 hours prior to the final intratracheal challenge of antigen. Goat IgG isolated from normal serum was used for treatment of control animals. BAL cells were harvested at 48 hrs post-challenge, at the peak of eosinophil infiltration, and differentially counted. In addition, lungs were inflated, fixed, and stored in 4% paraformaldehyde. Lung sections were examined histologically for cellular infiltration to determine the overall inflammation.

Measurement of Airway Hyperreactivity

By measuring the effects of antigen-challenge on airway hyperreactivity of subject mice, an accurate comparison can be made with airway hyperreactivity noted in human asthmatics. The subject mice are anesthetized with pentobarbitol (70–90 mg/kg, i.p.) and the jugular vein is cannulated with PE 10 silastic tubing. The trachea are then intibated with a specially angled 18 gauge needle, the chest opened, and the tubing connected to a Harvard ventilator (tidal volume=0.2 ml, frequency 120 breaths/min, positive end-expiratory pressure 2.5–3.0 cm $H_2O$) and placed in a whole body plethysmograph. This ventilation maintains normal arterial blood gases in the subject mouse. The dead space volume is 0.025 ml.

The mouse is placed within the main chamber along with a copper mesh, which serves as a heat sink to help maintain constant temperature. Since the box is a closed system, a change in lung volume is represented by a change in box pressure, which is measured by a sensitive transducer. The transducer is referenced to the pressure in an attached box to offset the effects of rapid ambient pressure fluxuations. A high resistance connection between the main box (mouse) and the reference box (control) with a time constant of approximately 4.5 seconds is used to equilibrate the pressures in the two boxes as the body temperature gradually heats the main chamber.

The system is also opened to ambient air through a valve with an even slower time constant (~11 seconds) to help keep the mean box pressure, which is the pleural pressure for the lung, close to zero.

The system is calibrated with a small syringe of a known volume of 0.2 ml, and at a frequency of about 120/min. A second transducer is used to measure pressure fluxuations at the opening of the tracheal tube, referenced to the body box or pleural pressure, therefore giving transpulmonary pressure (Ptp=airway pressure—box pressure). Ptp and box pressure is collected at 5 msec intervals during tidal breathing for several breaths over 10–15 seconds, and repeated three times for baseline measurements.

For methylcholine i.v. injection into the cannulated jugular vein, the measurements are taken for 30 seconds to assure that the results are captured during peak response. Ptp and box pressure are continually recorded on a chart recorder and at 5 msec intervals by a Macintosh Iici personal computer using an analog to digital data acquisition system (Strawberry Tree). The flow is then calculated as the change in volume from point to point/5 msec.

Resistance (R), lung conductance ($G_L=1/R$) and dynamic compliance ($C_{dyn}$) are calculated for the control period and at the peak response to methacholine. Resistance is derived from the difference in Ptp and airflow at mid-$V_t$ on inflation and deflation. The resistance of the tracheal tube is subtracted from all airway resistance measurements. Dynamic compliance is calculated as the change in $V_t$ divided by the difference between Ptp at end-inspiration and end-expiration when flow is zero.

Statistics. Statistical significance was determined by Student's t test and significance was determined with P values <0.05.

Results

Localization of the immune response to the airway induces an asthmatic-like reaction. Surprisingly, initial studies attempting to induce an asthmatic response by injecting SEA (10 μg in 25 μl of carrier) into the airways of SEA-sensitized mice demonstrated no increase in cellular infiltration, upon histological examination, and BAL cell analysis, as compared to the control vehicle challenged mice (data not shown). We therefore hypothesized that in order to initiate the allergic response, seen in asthma, a local pulmonary antigen exposure must occur prior to a secondary pulmonary challenge. To accomplish this, mice were first immunized i.p. with S. mansoni eggs, which secrete SEA, allowed to rest for 2 weeks followed by an intranasal challenge with 10 μg of SEA. The latter treatment allowed an initial pulmonary antigen exposure and localization of the SEA-specific, TH2 type response to the lungs. Six days after the intranasal challenge, mice were exposed to 10 μg of SEA (or vehicle saline control) into the airway via tracheostomy to initiate the antigen-driven airway inflammation. Histologically there was an intense accumulation of leukocytes within the interstitium of the lung beginning as early as 1 hour post final antigen exposure, peaking at 24–48 hours post-exposure (data not shown).

In addition, eosinophils were seen infiltrating the lung as early as 8 hr post-antigen challenge and continued to accumulate in peribronchial zones for the remaining 24–72 hours until harvesting. Vehicle treatment induced little cellular infiltration. These histological observations are similar to airway reaction associated with asthma in humans.

Accumulation of leukocytes in the lung and airway. The salient feature of airway inflammation associated with asthma in humans is the presence of interstitial and mucosal eosinophil rich infiltrates. To determine the cellular constituents of infiltrating leukocytes, BAL from SEA or vehicle challenged mice were collected in 1 ml aliquots of PBS with 50 mM EDTA. In addition, whole lungs were dispersed and cells differentially counted to assess leukocyte populations in the interstitium. The total number of cells in both the BAL and whole lung dispersements demonstrated a significant ($p<0.05$) increase in total cells in both compartments, interstitium and airway, of the lung, in response to SEA vs. vehicle control challenge. The cellular influx peaked at 8 hours and steadily declined to vehicle control levels at 48 hrs post-challenge in both the interstitial preparations and BAL samples.

FIG. 1A shows eosinophil infiltration into the lungs and airways. The graph shows eosinophil cell counts from dispersed lungs of SEA and vehicle trachea challenged mice. The collagenase dispersed lung cells were collected at 8, 24, and 48 hours after the antigenic challenge and quantitated by vital dye exclusion. Data represents the mean ± SE from 3 different mice in each group.

Figure 1B:
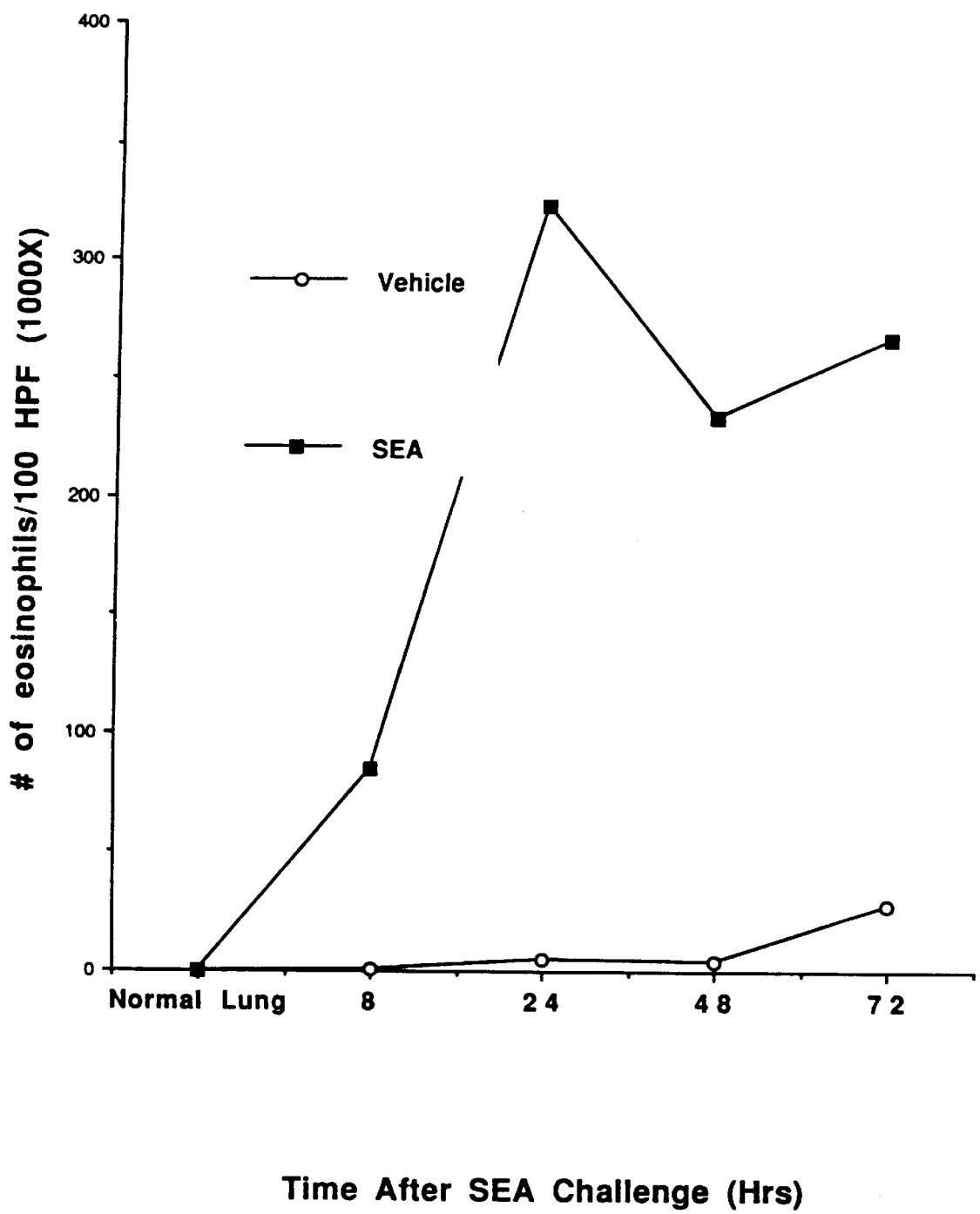
FIG. 1B demonstrates the morphometrics of eosinophils around the airways. The graph shows eosinophil accumulation around airways of SEA and vehicle challenged mice. The data for normal lung, and 8, 24, 48, 72 hours after challenge were scored as number of eosinophils per 100 HPF (high powered field) (1000×).

FIG. 1B demonstrates the morphometrics of eosinophils around the airways. The graph shows eosinophil accumulation around airways of SEA and vehicle challenged mice. The data for normal lung, and 8, 24, 48, 72 hours after challenge were scored as number of eosinophils per 100 HPF (high power field) (1000×).

We were next interested in the presence of individual cell populations. The kinetics of neutrophil recruitment within BAL demonstrated that these cells were most numerous at the earliest sampling point, 8 hrs, and declined thereafter. Although the SEA challenged mice had significantly higher levels of neutrophils, the same kinetic course was observed with the control vehicle (sterile saline) treated mice. In contrast, the accumulation of eosinophils followed a notably different pattern. After SEA airway challenge, the appearance of eosinophils in the BAL fluid was observed at 24 hrs and peaked at 48 hrs. Subsequently a decline in eosinophils in the BAL was observed at 72 hrs (24±12% of total cells) and 96 hrs (19±9.5% of total cells) post-exposure, yet substantial numbers of eosinophils were still evident. Control mice showed little evidence of eosinophil accumulation in the BAL fluid. These data suggest two phases of cellular recruitment: the first being a nonspecific neutrophil and the second a SEA-specific eosinophil infiltration compatible with airway inflammation of asthma.

The kinetics of leukocyte accumulation in the interstitium was also of interest. The dispersement of whole lungs from mice challenged as above allowed a single cell suspension to be assessed for total and differential cell counts. As in the BAL, neutrophils were most numerous in the lung interstitium early in the response at 8 hrs, and quickly declined at 24 and 48 hrs post challenge. As in the BAL, the total neutrophil accumulation (based on total cells) was greater in the SEA challenged than vehicle challenged lungs. The accumulation of eosinophils in the interstitial lung preparations again followed a different pattern of accumulation than seen for neutrophils. As shown in FIG. 1, eosinophils were initially found in both the SEA and vehicle challenged mice at low numbers. After 24 hrs, the SEA airway challenged mice had a significantly greater number of eosinophils as compared to vehicle controls. The SEA-induced interstitial eosinophilia at 48 hrs was lower than in corresponding BAL suggesting a movement of eosinophils from the interstitium to the airways.

Significantly it was also found that there was also an increase in large mononuclear cells in the lungs at 8 hr in SEA-challenged mice ($14.4±2.8×10^6$ cells/lung), as compared to vehicle challenged mice ($10.5±0.6×10^6$ cells/lung). Subsequently, lymphocytes were increased at 24 hrs in the SEA ($4.1±0.46×10^6$ cells/lung), as compared to the control ($2.7±0.45×10^6$ cells/lung) group. The presence of leukocytes at time 0, prior to the intratracheal challenge, was similar to background levels, with few neutrophils and eosinophils (data not shown). These data indicated a sequential infiltration of leukocytes into the SEA challenged lungs, with neutrophils and monocytic cells predominant at 8 hr, followed by increased numbers of lymphocytes and eosinophils at 24 hrs.

Figure 2A:
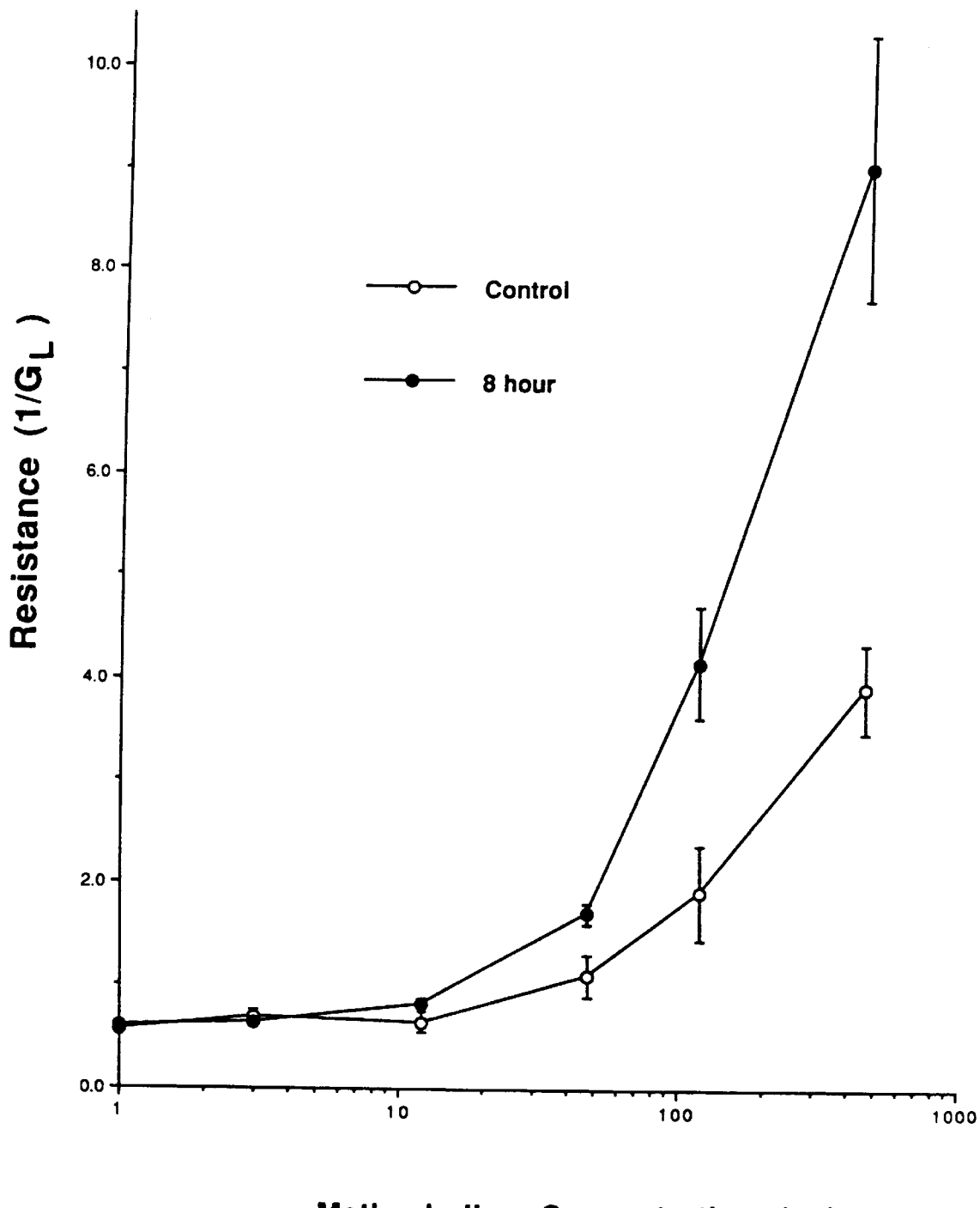
FIG. 2A shows airway hyperreactivity and increased resistance after SEA challenge, as measured at 8 hours. The graph shows that as methacholine concentration is increased ($\mu$g), the airway resistance ($1/G_L$) increases much more than that of the control vehicle challenged lung. Data represents 5 mice in each group.
Figure 2B:
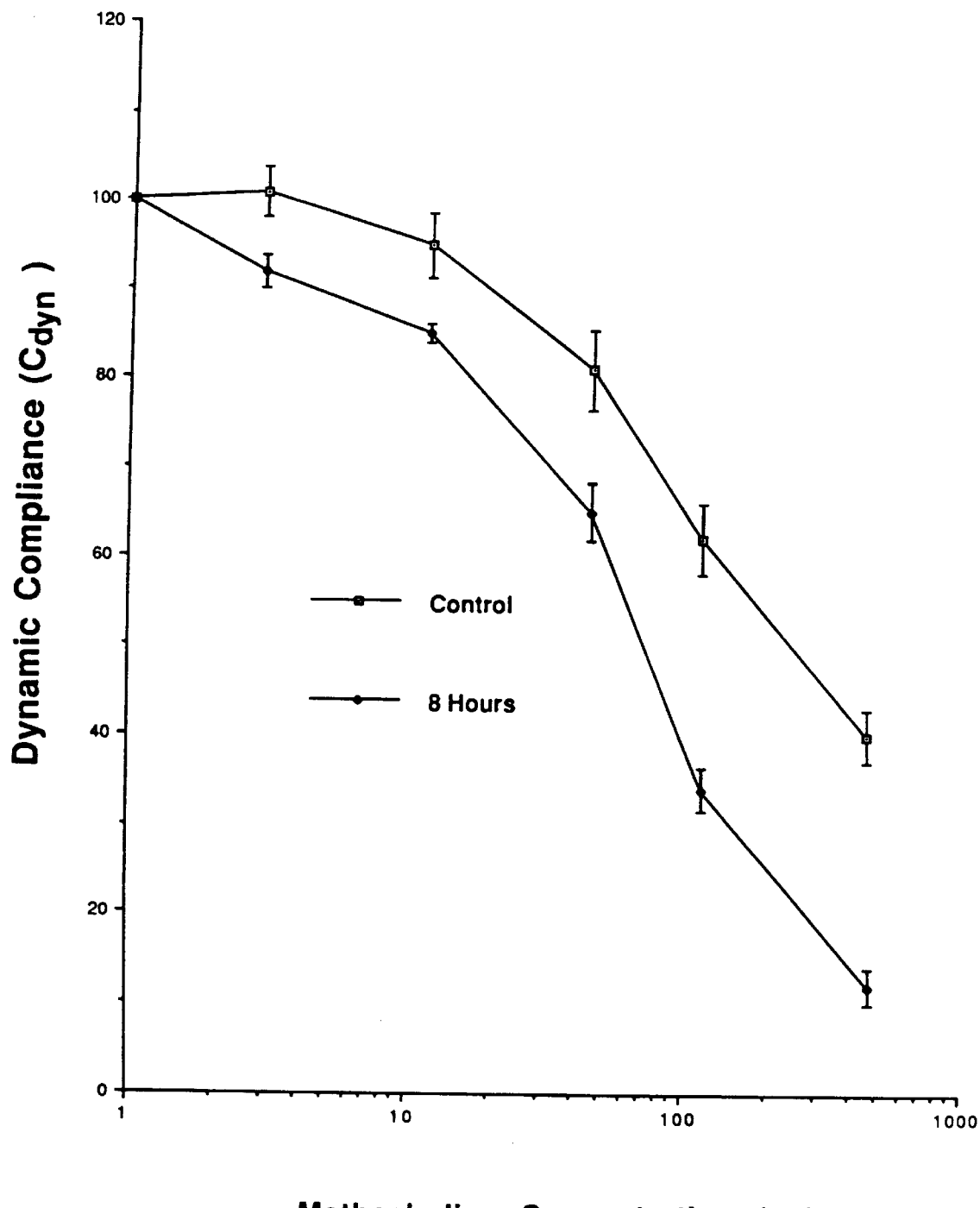
FIG. 2B shows airway hyperreactivity and decreased airway compliance after SEA challenge, as measured at 8 hours after challenge. The graph shows that as methacholine concentration increases ($\mu$g) the dynamic compliance of the lungs ($C_{dyn}$) decreases to a greater degree than control lungs. Data represents 5 mice in each group.

Physiological characterization of the model system reveals that the mice show associated airway reactivity, which is characteristic of the asthmatic response. FIG. 2A shows airway hyperreactivity and increased resistance after SEA challenge, as measured at 8 hours. The graph shows that as methacholine concentration is increased (pg), the airway resistance ($1/G_L$) increases much more than that of the control vehicle challenged lung. FIG. 2B shows airway hyperreactivity and decreased airway compliance after SEA challenge, as measured at 8 hours after challenge. The graph shows that as methacholine concentration increases ($\mu$g) the dynamic compliance of the lungs ($C_{dyn}$) decreases to a greater degree than control lungs. In addition, SEA, but not vehicle challenged mice demonstrated significant release of histamine at 1 hour post-challenge in BAL samples (data not shown).

Conclusion

A characteristic influx of eosinophils could be detected as early as 8 hrs with significant increases at 24–72 hrs post-challenge. An assessment of the bronchial alveolar lavage (BAL) fluid demonstrated dominant neutrophil infiltration at 8 hrs with a subsequent decrease to background by 48 hrs. In addition, peak monocyte infiltration occurred at 24 hrs and peak eosinophil extravasation into the airway was shown at 48 hrs. The examination of leukocyte infiltrates in the interstitium in dispersed lung preparations again demonstrated early neutrophil and monocyte infiltration at 8 hours post-challenge with increases in lymphocyte and eosinophil infiltrates at 24 hrs. The data presented defines a murine model of airway inflammation comparable with that found in human asthma.

EXAMPLE 2

IL-4 and Eosinophil infiltration

Since IL-4 is an important inflammatory cytokine produced during antigen-specific immune responses and has been implicated in asthmatic responses, we next examined BAL fluid for the presence of IL-4 after antigen challenge. IL-4 levels (Table 1) were detected in the BAL fluid at 8 hrs post-SEA challenge, with sustained levels observed at 24 and 48 hrs. These levels preceded the peak eosinophil influx that occurred at 48 hrs.

Interestingly, IL-4 levels began to decrease by 48 hrs and were undetectable in 72 hr (<1 unit/ml) BAL fluid. The decline in IL-4 correlated with the diminished eosinophil levels found. In contrast, IL-4 was undetectable in the BAL of vehicle control-challenged mice at all time points.

TABLE 1

| IL-4 Levels in BAL fluid from asthmatic mouse model | | |
|---|---|---|
| Time of Response | IL-4 Production (units/ml)* | |
| (Hours) | Vehicle | SEA |
| 8 | <1 | 10.5 ± 4.2 |
| 24 | <1 | 9.4 ± 1.7 |
| 48 | <1 | 7.4 ± 2.2 |

*The mean ± SEM from 5–6 BAL sample/time point

Figure 3:
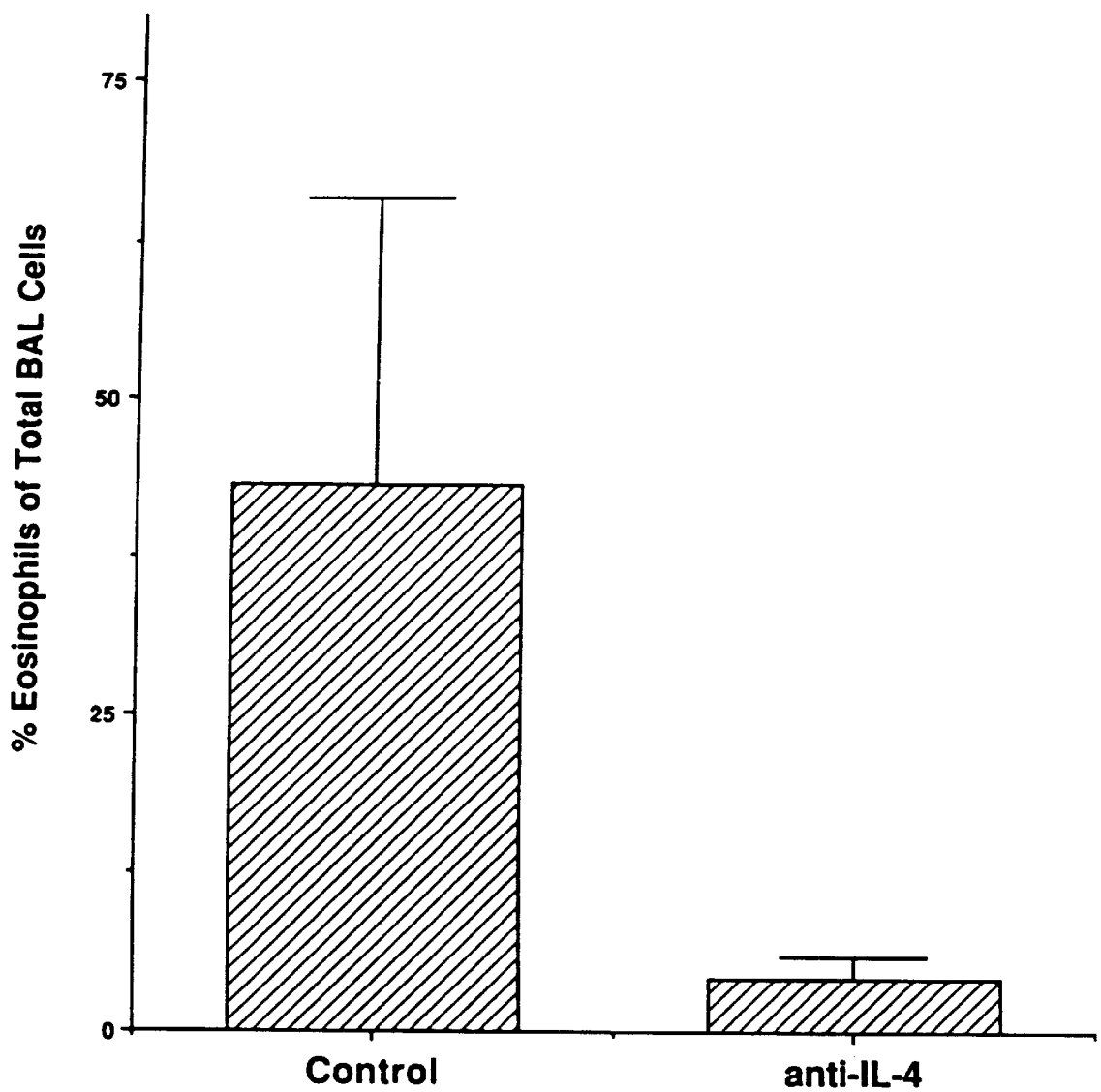
FIG. 3 is a graph which shows that anti-IL-4 administration reduced eosinophilia.

To determine whether IL-4 directly participated in the eosinophil infiltration of the lung, we passively immunized mice with anti-IL-4 polyclonal antibodies in vivo 4 hrs prior to the SEA tracheal challenge. Subsequent examination of peak eosinophil influx at 48 hrs demonstrated a ten-fold decrease in eosinophil influx in mice treated with anti-IL-4 antibodies as compared with those that were untreated (FIG. 3).

Furthermore, dispersed lungs from anti-IL-4 and control animals demonstrated a diminished inflammatory response as determined by total cell influx ($11.8\pm2.1\times10^6$ versus $18.7\pm1.3\times10^6$ total cells, respectively). These results demonstrated that IL-4, produced early in the response, plays a major role in eosinophil recruitment and the overall inflammation associated with asthmatic lung reactivity.

Examination of IL-4 production in the BAL fluid demonstrated the presence of IL-4 early in the response with levels peaking between 8 and 24 hrs post antigen challenge with no detectable IL-4 in the saline vehicle challenged mice. Mice treated with anti-IL-4 antibodies demonstrated a tenfold decrease in BAL eosinophil influx at 48 hrs post-challenge and a reduction in total pulmonary leukocyte cellularity. These studies demonstrate an IL-4 dependent mechanism for the induction of eosinophil recruitment.

Conclusion

We have described a murine model of asthma which is based upon the development of TH2 type-eosinophilic response to a soluble antigen preparation from *Schistosoma mansoni* eggs (soluble egg antigen, SEA) localized to the airway. Because SEA has previously been described as inducing primarily a TH2 type response, its use as an immunogen in the present model is consonant with findings in human asthma. With this model we have determined the sequence of leukocyte infiltration into the lung interstitium and airway as well as demonstrated airway reactivity associated with SEA challenge. These results indicate that the leukocyte infiltration begins with neutrophil accumulation, peaking at 8 hr, followed by mononuclear cell and eosinophil infiltration into the lung interstitium. Subsequently, accumulation of neutrophils, mononuclear cells and eosinophils in the airways peaked at 8 to 24 and 24 to 48 hr post-antigen challenge, respectively. In addition, IL-4 production correlated with the leukocyte recruitment, while in vivo neutralization of IL-4 greatly diminished eosinophil influx into the BAL, thus demonstrating an integral role for this cytokine in the leukocyte recruitment response associated with asthma.

EXAMPLE 3

SCF and Asthma

The murine model of the instant invention, described above, was further utilized to demonstrate the effect of administration of polyclonal anti-SCF, via tracheal administration, would have on subsequent asthma associated inflammation.

Materials and Methods

Animals

Female CBA/J misc were purchased from Jackson Laboratories, (Bar Harbor, Me.) were maintained under standard pathogen-free conditions.

Egg isolation and SEA protein preparation

Soluble egg antigens (SEA) were prepared from acutely *S. mansoni*-infected mice as previously describe. Briefly, eggs were isolated from livers of infected mice after a 3 day incubation and ground on ice to release the soluble antigens from the egg. The preparation was then spun in an ultracentrifuge at 1000,000×G for 2 hrs and the supernatant collected. The antigens in the supernatant are primarily glycoproteins which have been characterized as inducing a TH2 type granulomatous response in schistosomiasis.

Sensitization and induction of the airway response

In order to induce a TH2 type response the following procedure was established in normal CBA/J mice as previously described above. Briefly, the mice were immunized with 5000 isolated *S. mansoni* eggs i.p. at days 0 and 7 of the protocol. On day 14 the mice were given an intranasal challenge of 10 $\mu$g of SEA in 10 $\mu$l of PBS to localize the response to the airway. This initial intranasal challenge with antigen induced little cellular infiltrate into the lungs of the mice upon histological examination. Mice were then rechallenged six days later by intratracheal administration of 10 $\mu$g of SEA in 25 $\mu$l of sterile PBS or with PBS alone (vehicle). The magnitude of infiltration in both the vehicle control and SEA challenged mice was examined histologically. Only the SEA-challenged mice displayed a significant inflammatory response which included neutrophil and eosinophil infiltration as previously described.

Quantification and differentiation of leukocyte populations in BAL and lungs

Mice immunized and challenged with SEA or saline vehicle, were subjected to a 1 ml bronchoalveolar lavage (BAL) with phosphate buffered saline (PBS) containing 50 mM EDTA at various time points post-challenge. The lungs were removed after the 1 ml PBS-EDTA lavage and dispersed with collagenase (0.2%, Type IV, Sigma) as previously described. The dispersed cells were then counted, dispersed using a cytospin and differentially stained with Wright-Giemsa stain. The cell types (mononuclear phagocytes, lymphocytes, neutrophils, and eosinophils) were expressed as a percentage based on 200 total cells counted/sample.

Lung homogenates

Isolated whole lung tissue was homogenated on ice using a tissue-tearor (Biospec Products, Racine, Wis.) for 30 seconds in 1 ml of PBS containing 0.05% Triton X-100. Previous results indicate that there was no interference in ELISA measurements with this buffer. The resulting supernatant was isolated after a high-speed spin (10,000×g) and subsequent filtration through a 1.2 micron syringe filter (Gelman Sciences, Ann Arbor, Mich.). The resultant supernatants were immediately frozen at −70° C. until tested in the MIP-1α ELISA.

SCF ELISA

SCF was quantitated by ELISA using a modification of a double ligand method. Briefly, flat-bottomed 96 well microtiter plates (Nunc Immuno-Plate 196-F, Denmark, Netherlands) were coated with 50 $\mu$l/well of rabbit anti-SCF antibody (Genzyme,) (1 ng/$\mu$l in 0.6M NaCl, 0.26M $H_3BO_4$, and 0.03N NaOH, pH 9.6) for 16 hrs at 4° C. and then washed with phosphate buffered saline (PBS), pH 7.5, 0.05% Tween-20 (wash buffer). Nonspecific binding sites were blocked with 2% BSA in PBS and incubated for 90 min at 37° C. Plates were rinsed four times with wash buffer and diluted (1:2 and 1:10) cell-free supernatants in duplicate were added, followed by incubation for 1 hr at 37° C. Plates were washed four times followed by the addition of 50 $\mu$l/well biotinylated rabbit anti-SCF antibody (Genzyme, 3.5 ng/$\mu$l in PBS, pH 7.5, 0.05% Tween-20, and 2% FCS), and plates incubated for 30 min at 37° C. Plates were washed four times, streptavidin-peroxidase conjugate (Bio-Rad Laboratories, Richmond, Calif.) added, and the plates incubated for 30 min at 37° C. Plates were again washed four times and chromogen substrate (Bio-Rad Laboratories, Richmond, Calif.) added. The plates were then incubated at room temperature to the desired extinction, and the reaction terminated with 50 $\mu$l/well of 3M $H_2SO_4$ solution. Plates were read at 490 nm in an ELISA reader. Standards were ½ log dilutions of recombinant SCF from 10 ng/ml to 100 ng/ml. This ELISA method consistently detected SCF concentrations above 250 ng/ml. The SCF antibody ELISA did not cross-react with hSCF, MIL-3, mIL-1α, mTNF, mMIP-1α, IL-6, mJE, MmIP-1β, hMCP-1, hiL-8, hRANTES, hMIP-1α, hTNF, and hMIP-1β.

In vivo neutralization of SCF

Neutralization of SCF was carried out using a polyclonal anti-SCF antibody (Genzyme). The anti-SCF or control antibody was administered intratracheally with SEA at time 0. The BAL fluid was harvested at 48 hrs post-SEA challenge and analyzed for the leukocyte infiltration. In additional studies, anti-SCF was administered into the airway and BAL harvested at 1 hr post-challenge for histamine assay as an indicator of mast cell degranulation.

Immunohistochemical localization of SCF

Paraffin embedded tissue sections were mounted on poly-L-lysine coated slides, deparaffinized with xylene, and stepwise rehydrated in 100%, 95%, 70%, and 50% ethanol followed by a 10 minute incubation in PBS. Cells from BAL fluid were prepared by cytospin onto poly-L-lysine coated slides, followed by a 10 minute fixation in 4% paraformaldehyde. All tissue sections and fixed cells were blocked with normal goat serum for 30 minutes. The sections were stained by covering with rabbit anti-murine SCF serum (diluted 1:250 in PBS) for 30 minutes at 37° C. After rinsing the sections 3 times with PBS, the sections were overlaid with supersensitive reagent diluted 1:30 in PBS, containing biotinylated goat-anti-rabbit IgG (Biogenex, San Ramon, Calif.) for 20 minutes. After rinsing 3 times with PBS, the sections were incubated for 20 minutes with streptavidin-peroxidase (Biogenex, 1:1000) at 37° C. The slides were rinsed with PBS and overlaid with AEC solution until color development was observed (about 10–20 minutes). Sections were rinsed and counterstained with Mayer's hemotoxylin.

Statistics

Statistical significance was determined by Student's t test and significance was determined with P values<0.05.

Results

Increased SCF mRNA expression and protein production during allergic airway inflammation SCF has demonstrated multiple roles in mast cell activation and may be especially pertinent in an allergic inflammatory model. To determine whether SCF mRNA expression as increased during antigen-specific inflammation we performed RT-PCR on cDNA made from whole lung RNA. Low expression was observed in unimmunized control lung RNA which greatly increased in the immunized control lung which had been challenged by an intranasal SEA treatment, but not rechallenged intratracheally. Interestingly, upon SEA or vehicle rechallenge intratraecheally there neither appeared to be an increase in the mRNA expression over that observed in the immunized control nor was there a significant increase in the SEA vs. vehicle challenge.

Figure 4:
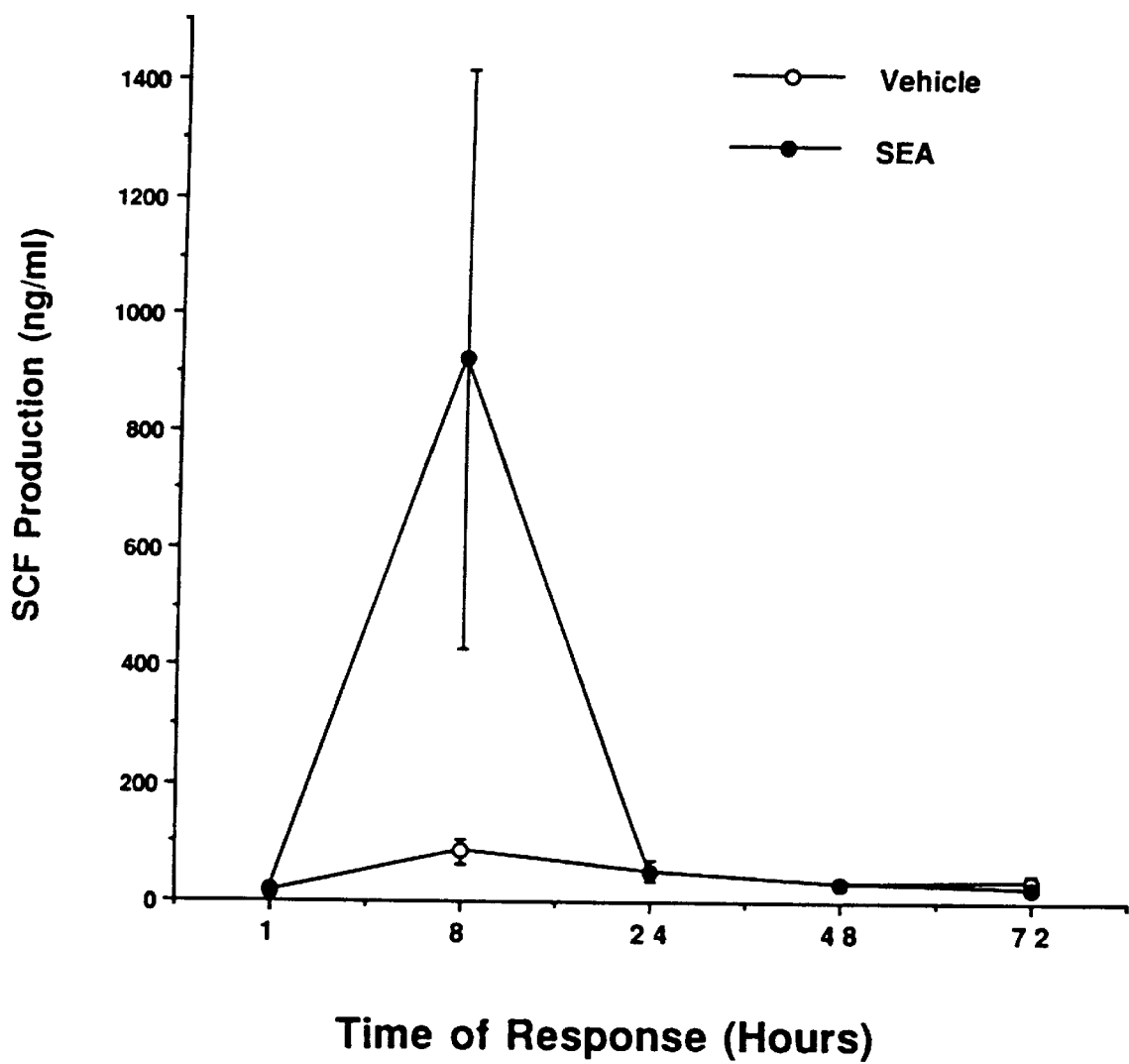
FIG. 4 is a graph which shows the production of SCF in response to SEA or vehicle challenge as measured at 1, 8, 24, 48, and 72 hours after challenge. Data represents 6 mice in each group.

To ascertain the level of SCF in the lungs of these immunized and rechallenged mice we measured specific protein by ELISA in whole lung homogenates. Control background levels of SCF in lungs from normal mice were 21.4±2.4 ng/ml. A similar level of SCF was observed in immunized, nonchallenged control mice. The SCF levels in lungs from SEA challenged mice rose significantly (≈10 fold increase) over the background levels and the vehicle control levels, peaking at 8 hrs, before falling to vehicle control levels at 24 hrs post-SEA challenge (FIG. 4). When SCF in the serum from these same mice were assayed in the ELISA a similar time course of production was observed, peaking at 8 hrs post-SEA challenge, however, with a reduced magnitude as compared to the lung. FIG. 4 is a graph which shows the production of SCF in response to SEA or vehicle challenge as measured at 1, 8, 24, 48, and 72 hours after challenge. These studies demonstrated that SCF was increased antigen-specifically in immunized mice.

Figures 5A, 5B:
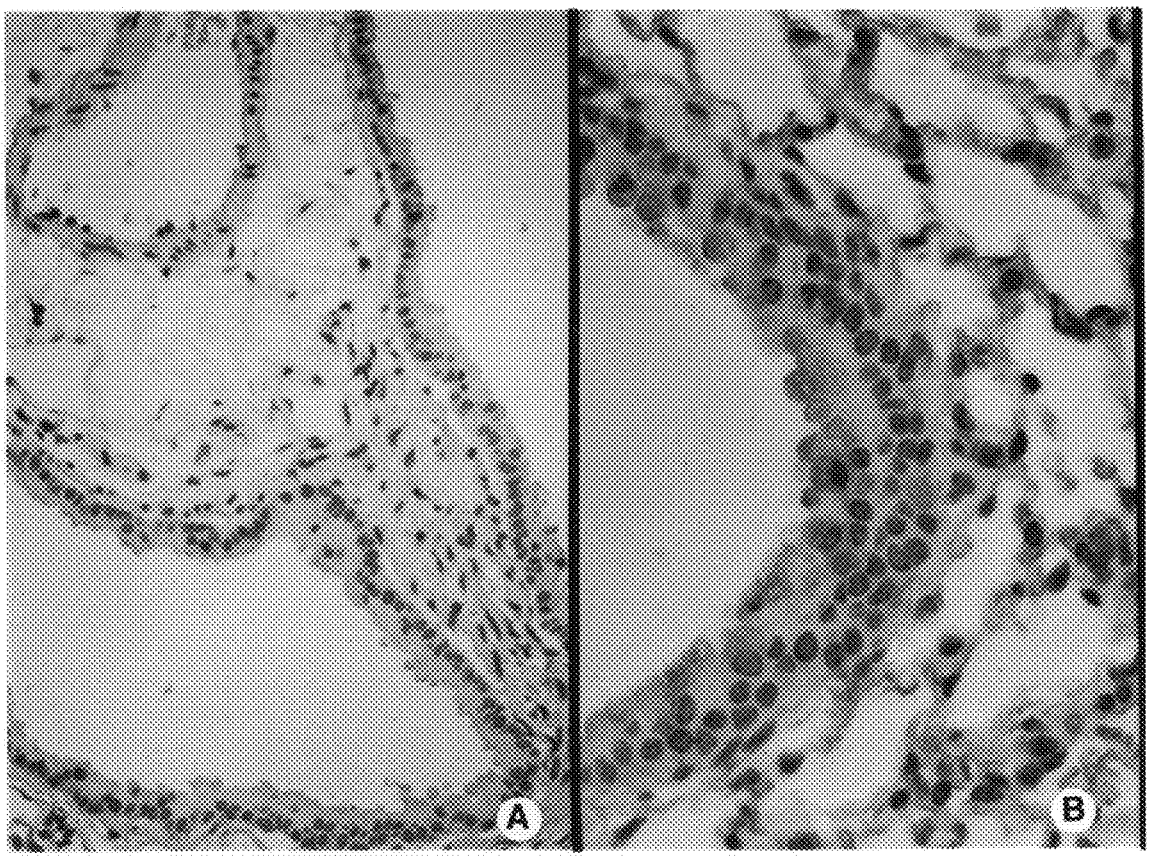
FIG. 5(A–C) demonstrates immunostaining of allergen-challenged lung for SCF (FIG. 5B & FIG. 5C); in particular Lung and airway epithelial cells and Macrophages. Control antibody staining (FIG. 5A) demonstrated no nonspecific localization.
Figure 5C:
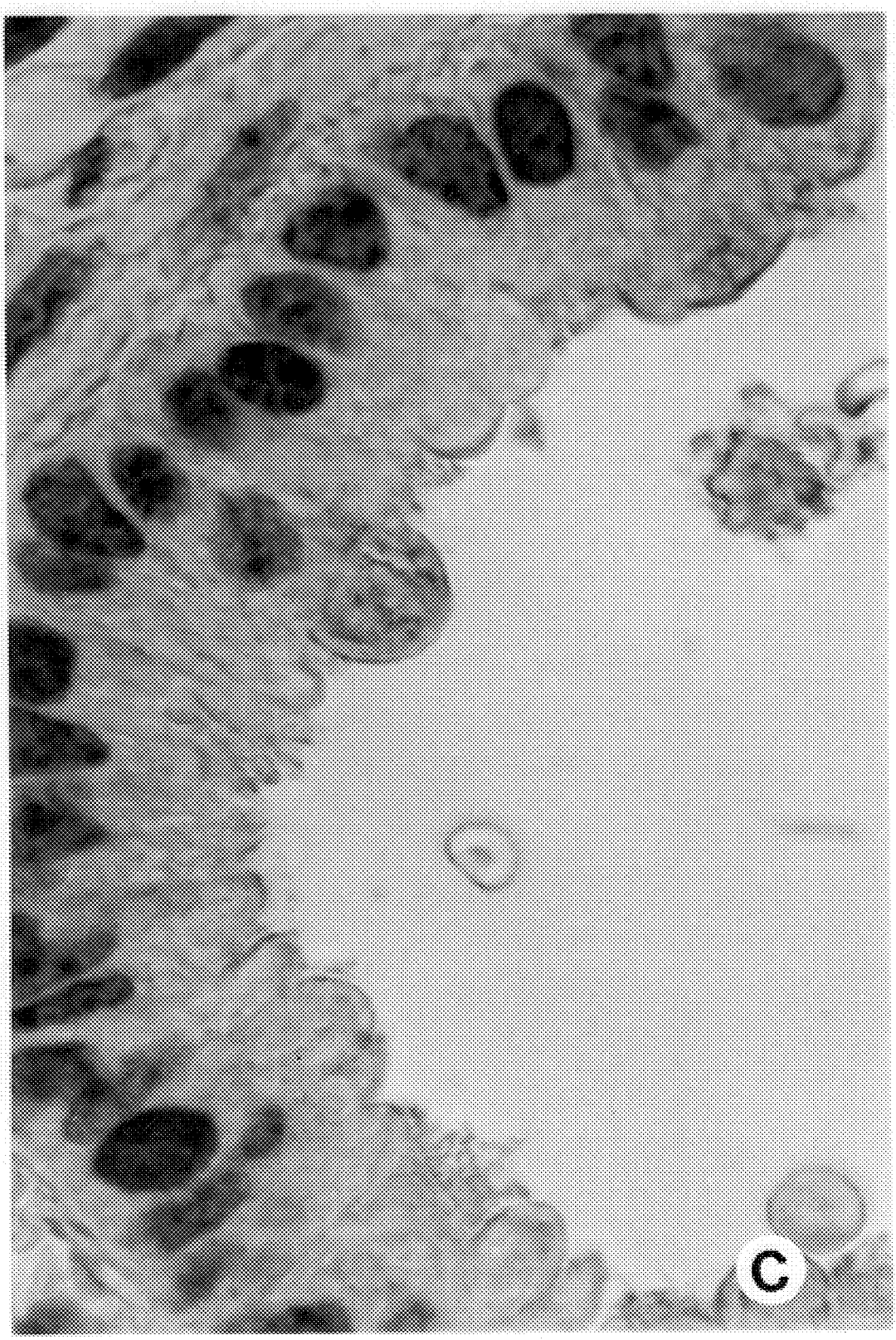
Figures 6A, 6B:
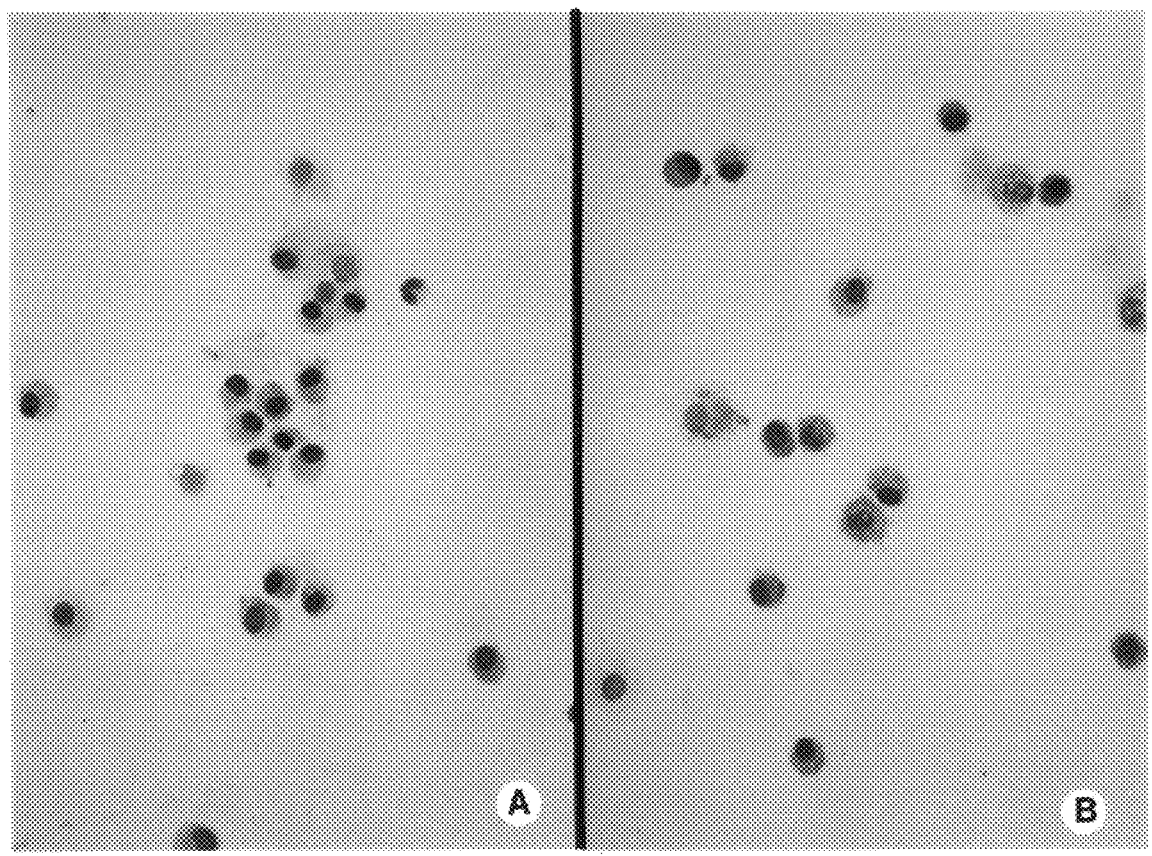
FIG. 6 (A–B) demonstrates immunostaining of BAL cells for SCF (FIG. 6B), in alveolar macrophages. Control antibody staining demonstrated no nonspecific staining (FIG. 6A).

Lung sections and BAL cells, immunostained for SCF production reveals that the cells which are strongly positive, are type II epithelial cells and macrophages. FIG. 5 demonstrates immunostaining of allergen challenged lung cells for SCF, in particular lung and airway epithelial cells and macrophages. FIG. 6 demonstrates immunostaining of BAL cells for SCF, in alveolar macrophages.

Inhibition of eosinophilic airway inflammation by neutralization of SCF

Figure 7:
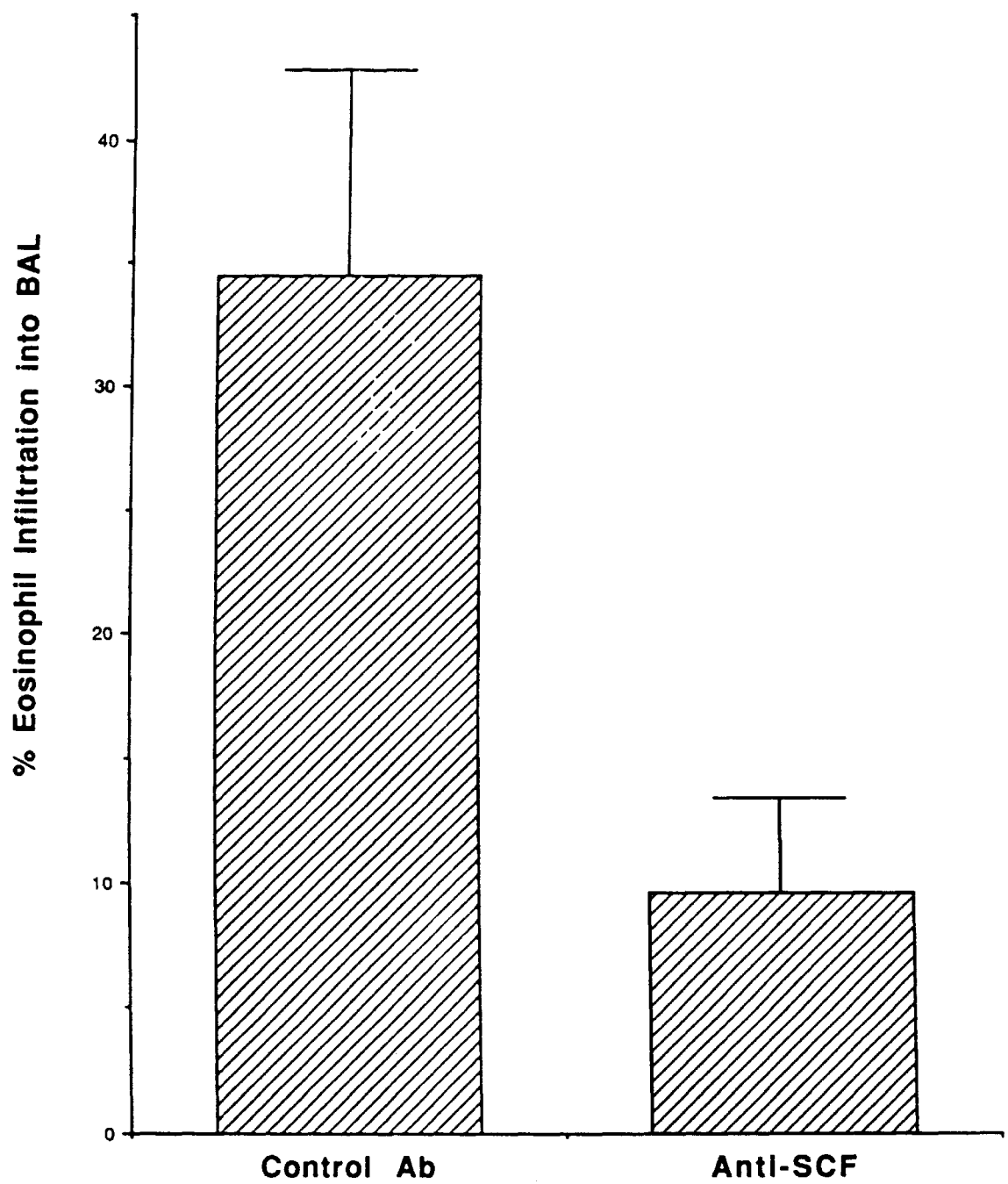
FIG. 7 is a graph which shows the effect of anti-SCF administered along with intratracheal SEA challenge as expressed in 1% eosinophils of total BAL leukocytes. Anti-SCF blocks eosinophil influx into the airspace when injected intratracheally, but not when administered interperitoneally (i.p. data not shown). Data represents 12 mice in each group.

To determine the role of SCF in vivo, sensitized mice were intratracheally challenged with SEA in the presence of anti-SCF antibody or control antibody. The eosinophil recruitment in sensitized mice was examined at 48 hrs post-SEA challenge, the time of peak eosinophil recruitment. The data indicates that inhibition of SCF significantly decreased the influx of eosinophils into the airway (>50%) as compared to the control antibody treated group. FIG. 7 is a graph which shows the effect of anti-SCF administered along with intratracheal SEA challenge as expressed in % eosinophils of total BAL leukocytes. Anti-SCF blocks eosinophil influx into the airspace when injected intratracheally, but not when administered interperitoneally (i.p. data not shown).

Conclusions

These studies indicated that SCF played an activational role in the airway inflammation model which culminates in eosinophil inflammation and that administration of anti-SCF can serve as an effective therapeutic treatment for asthma.

It should be understood that the foregoing disclosure emphasizes certain specific embodiments of the invention and that all modifications or alternatives equivalent thereto are within the spirit and scope of the invention as set forth in the appended claims.

We claim:

1. A method for inhibition of eosinophil infiltration to the lung in mammals, by inhibiting interaction between Stem Cell Factor (SCF) and SCF-receptor protein, comprising contacting lung tissue by intra-tracheal administration with an antibody or antigen binding fragment thereof, wherein said antibody or antigen binding fragment thereof specifically binds with SCF, said binding inhibiting the interaction between SCF and SCF-receptor protein, such that antigen stimulated eosinophil infiltration to the lung is effectively inhibited.

2. A method as in claim 1 wherein the said antibody or antigen binding fragment thereof, is polyclonal.

3. A method as in claim 1 wherein said antibody or antigen binding fragment thereof, is monoclonal.

* * * * *